(12) United States Patent
Carter

(10) Patent No.: US 7,825,083 B2
(45) Date of Patent: Nov. 2, 2010

(54) SYNOVIAL FLUID BARRIER

(75) Inventor: Andrew Carter, Trumbull, CT (US)

(73) Assignee: Spine Wave, Inc., Shelton, CT (US)

( * ) Notice: Subject to any disclaimer, the term of this patent is extended or adjusted under 35 U.S.C. 154(b) by 1659 days.

(21) Appl. No.: 11/055,331

(22) Filed: Feb. 10, 2005

(65) Prior Publication Data
US 2006/0178743 A1    Aug. 10, 2006

(51) Int. Cl.
C07K 14/78    (2006.01)
A61K 38/00    (2006.01)

(52) U.S. Cl. .................. 514/2; 424/520; 424/9.322; 530/352; 530/350

(58) Field of Classification Search .................. None
See application file for complete search history.

(56) References Cited

U.S. PATENT DOCUMENTS

| | | | |
|---|---|---|---|
| 4,187,852 A | 2/1980 | Urry et al. | |
| 4,589,882 A | 5/1986 | Urry | |
| 4,595,713 A * | 6/1986 | St. John | 523/105 |
| 4,898,926 A | 2/1990 | Urry | |
| 5,064,430 A | 11/1991 | Urry | |
| 5,235,041 A | 8/1993 | Cappello et al. | |
| 5,243,038 A | 9/1993 | Ferrari et al. | |
| 5,292,362 A | 3/1994 | Bass et al. | |
| 5,336,256 A | 8/1994 | Urry | |
| 5,374,431 A | 12/1994 | Pang et al. | |
| 5,496,712 A | 3/1996 | Cappello et al. | |
| 5,514,581 A | 5/1996 | Ferrari et al. | |
| 5,770,697 A | 6/1998 | Ferrari et al. | |
| 5,800,544 A | 9/1998 | Demopulos et al. | |
| 5,817,303 A * | 10/1998 | Stedronsky et al. | 424/78.02 |
| 5,853,746 A | 12/1998 | Hunziker | |
| 6,018,030 A | 1/2000 | Ferrari et al. | |
| 6,033,654 A | 3/2000 | Stedronsky et al. | |
| 6,080,192 A | 6/2000 | Demopulos et al. | |
| 6,080,194 A | 6/2000 | Pachence et al. | |
| 6,106,556 A | 8/2000 | Demopulos et al. | |
| 6,140,072 A | 10/2000 | Ferrari et al. | |
| 6,184,348 B1 | 2/2001 | Ferrari et al. | |
| 6,355,776 B1 | 3/2002 | Ferrari et al. | |
| 6,376,742 B1 | 4/2002 | Zdrahala et al. | |
| 6,380,154 B1 | 4/2002 | Cappello et al. | |
| 6,403,637 B1 | 6/2002 | Partridge | |
| 6,423,333 B1 | 7/2002 | Stedronsky et al. | |
| 6,454,811 B1 * | 9/2002 | Sherwood et al. | 623/23.76 |
| 6,458,889 B1 | 10/2002 | Trollsas et al. | |
| 6,511,511 B1 | 1/2003 | Slivka et al. | |
| 6,530,956 B1 | 3/2003 | Mansmann | |
| 6,531,147 B2 | 3/2003 | Sawhney et al. | |
| 6,630,457 B1 | 10/2003 | Aeschilmann et al. | |
| 6,656,925 B2 | 12/2003 | Petrus | |
| 6,835,377 B2 * | 12/2004 | Goldberg et al. | 424/93.7 |
| 7,217,294 B2 * | 5/2007 | Kusanagi et al. | 623/18.11 |
| 7,235,074 B1 * | 6/2007 | Sklar | 606/53 |
| 7,252,832 B1 * | 8/2007 | Stone et al. | 424/422 |

| | | | |
|---|---|---|---|
| 2002/0082220 A1 | 6/2002 | Hoemann et al. | |
| 2002/0119952 A1 | 8/2002 | Petrus | |
| 2002/0122790 A1 | 9/2002 | Hunziker | |
| 2002/0123805 A1 * | 9/2002 | Murray et al. | 623/13.17 |
| 2002/0173855 A1 | 11/2002 | Mansmann | |
| 2002/0187182 A1 | 12/2002 | Kramer et al. | |
| 2003/0075822 A1 | 4/2003 | Slivka et al. | |
| 2003/0104589 A1 | 6/2003 | Stedronsky et al. | |
| 2003/0224989 A1 | 12/2003 | Quinn et al. | |
| 2003/0235589 A1 | 12/2003 | Demopulos et al. | |
| 2004/0059416 A1 * | 3/2004 | Murray et al. | 623/13.15 |
| 2004/0228901 A1 * | 11/2004 | Trieu et al. | 424/426 |
| 2005/0216014 A1 * | 9/2005 | May et al. | 606/72 |

FOREIGN PATENT DOCUMENTS

| | | |
|---|---|---|
| EP | 0 528 080 | 2/1993 |
| JP | 4334396 | 11/1992 |
| WO | WO 93/04711 | 3/1993 |
| WO | WO 94/01508 | 1/1994 |
| WO | WO 95/05396 | 2/1995 |
| WO | WO 96/34618 | 11/1996 |
| WO | WO 02/28417 | 4/2002 |

OTHER PUBLICATIONS

Acharya et al. (2008) Silk fibroin protein from mulberry and non-mulberry silkworms: cytotoxicity, biocompatibility and kinetics of L929 murine fibroblast adhesion, J. Mater. Sci. Mater. Med., vol. 18, No. 8, pp. 2827-2836.*
Friedel et al. (2005) Fabrication of polymer derived ceramic parts by selective laser curing, J. Eur. Ceram. Soc., vol. 25, pp. 193-197.*
Convery et al.; The Repair of Large Osteochondral Defects; Clinical Orthopedics and Related Research vol. 82, pp. 253-262; 1972.
Knight et al.; Genetically Engineered, Enzymatically Crosslinked Elastinlike Polypeptide Gels for Cartilage Tissue Repair; Transactions of the Society for Biomaterials vol. 26, pp. 54, 2003.
Betre et al.; Genetically engineered Elastin-like Polypeptide Promotes Chondrocytic Differentiation of the Human Adipose Tissue-Derived Adult Stem Cells in Vitro; Transactions of the Orthopedic Research Society, vol. 29, pp. 158, 2004.
Fernandes et al.; The role of cytokines in osteoarthritis pathophysiology; Bioheology, vol. 39, Issue 1-2, pp. 237-246; 2002.
Sierra; Fibrin Sealant Adhesive Systems; A review of Their Chemistry, Material Properties and Clinical Applications; J. Biomat. App., vol. 7, pp. 309-352, 1993.

(Continued)

*Primary Examiner*—Anand U Desai
*Assistant Examiner*—Samuel Liu
(74) *Attorney, Agent, or Firm*—Hoffmann & Baron, LLP

(57) ABSTRACT

A composite tissue formed in situ is provided. The composite tissue includes a synovial joint tissue; and a barrier material adhered thereto for sealing the synovial joint tissue against synovial fluid. Also provided is a method for regenerating synovial joint tissue in situ by excluding synovial fluid therefrom. The method includes providing a synovial joint tissue having a defect; and placing a barrier material in intimate contact with the defect for sealing the defect against synovial fluid. The barrier material includes a curable protein copolymer. The method further includes curing the protein copolymer in situ. The barrier material can include a crosslinked network, or a self gelled network of repeating elastin-like and fibroin-like polymer chains.

8 Claims, No Drawings

OTHER PUBLICATIONS

Bryant et al.; Controlling the spatial distribution of EMC components in degradable PEG hydrogels for tissue engineering cartilage; J. Biomed Res. vol. 64A, Issue 1, p. 70-79; Jan. 1, 2003.

Temenoff et al.; Effect of drying history on swelling properties and cell attachment to oligo(poly(ethylene glycol) fumarate) hydrogels for guided tissue regeneration applications; J. Biomater. Sci. Polym Ed.; vol. 14, Issue 9, pp. 989-1004; 2003.

Sims et al.; Injectable Cartilage Using Polyethylene Oxide Polymer Substrates; Plastic Reconstr. Surg., vol. 98, Issue 5, pp. 843-850; 1996.

Lee et al.; The effects of cross-linking of collagen-glycosaminoglycan scaffolds on compressive stiffness, chondrocyte-medicated contraction, proliferation and biosynthesis; Biomaterials, vol. 22, Issue 23, pp. 3145-2154; Dec. 2001.

Chenite et al.; Novel injectable neutral solutions of chitosan form biodegradable gels in situ; Biomaterials; vol. 21, issue 21, pp. 2155-2161; 2000.

Paige et al; Injectable Cartilage; Plast. Reconstr. Surg.; vol. 96; issue 6, pp. 1390-1398; Nov. 1995.

Nettles et al.; Photocrosslinkable Hyaluronan as a Scaffold for Articular Cartilage Repair; Ann Biomed Engin.; vol. 32, Issue 3, pp. 391-397; Mar. 2004.

Betre et al.; Characterization of a Genetically Engineered Elastin-like Polypeptide for Cartilaginous Tissue Repair; Biomacromolecules; vol. 3, issue 5, pp. 910-916; Sept.-Oct. 2002.

Hangody et al; MosaicPlasty™ Osteochondral Grafting Technique Guide, Arthroscopic Technique; Smith & Nephew, Inc. Copyright 1999 pp. 3-10.

Carticel: The Cost of this Alternative Therapy; http://biomed.brown.edu/Courses/BI108_1999_Groups/Cartilage_Team/matt/Carticel1.html; Dec. 30, 2004.

Genzyme Tissue Repair; http://arthroscopy.com/sp08001.htm; Dec. 30, 2004.

Gill et al.; The mechanism of the Microfracture Technique; http://www.sofarthro.com/ANNALES/ANNALES_1999/CARTILAGE/Microfracture.htm Oct. 19, 2004.

Cawston et al.; Mechanisms of Cartilage Breakdown and Repair; http://www.arc.org.uk/about_arth/med_reports/series3/tr/6415.htm; Dec. 30, 2004.

* cited by examiner

SYNOVIAL FLUID BARRIER

FIELD OF THE INVENTION

The present invention relates to methods and compositions for the treatment and repair of injured synovial joint tissue. In particular, the invention relates to the use of a barrier material including a network of polymer chains for sealing synovial joint tissue against synovial fluid during healing of the joint tissue.

BACKGROUND OF THE INVENTION

It is well documented that injured articular cartilage has only a limited ability for self-repair. Since articular cartilage is relatively avascular and aneural, loss of surface tissue will result in a permanently scarred site. Lesions which fracture subchondral bone, which has a greater vascular supply, will undergo an inflammation/repair response, with the damaged site filling with fibrocartilage tissue (Convery, et al. (1972) Clinical Orthopedics and Related Research 82:253-262). In either case, function is impaired and chronic pain is the usual prognosis, since the biochemical and biomechanical characteristics of the cartilage have been altered.

There are a number of different strategies that are used in cartilage repair. For example, microfracture, or Pridie drilling is often utilized. In this treatment, holes are created either by drilling or with a pick through the subchondral bone into the underlying cartilage. The holes allow stem cells from the bone marrow to enter the defect site and clot, and then form a repair tissue. This repair is generally found to result in a poor quality tissue, which breaks down with time.

Alternatively, surgeons have used Mosaicplasty™. In this technique, plugs of cartilage and bone are taken from the periphery of the joint and placed in the defect site. This technique has enjoyed some success, but is surgically very demanding and leaves donor tissue harvest sites which have some morbidity.

Autologous tissue engineering approaches have also been used in cartilage repair. For example, Carticel™ employs a commercial process to grow (culture) a patient's own (autologous) cartilage cells, known as chondrocytes, for use in treating damaged articular cartilage of the knee. Once the patient's cells are expanded in culture, they are reimplanted in the patient. The cells are held in place by a patch of periosteum, which is sutured in place, and then sealed to prevent cell migration using fibrin glue. This approach is very expensive, and is also surgically very demanding.

Other techniques for cartilage repair utilize growth factors and other signaling molecules. However, these techniques are still in the research phase, and have not been clinically proven.

Injectable, in situ polymerizing or crosslinking biomaterials have been used previously as defect-filling scaffolds for cartilage repair (Bryant, et al. J. Biomed Res., Jan. 1 2003, 64A(1), pp. 70-9; Temenoff, et al. J. Biomater. Sci. Polym Ed., 2003, 14(9), pp. 989-1004 and Sims, et al. Plast Reconstr., Surg., 1996, 98(5) pp. 843-50). These biomaterials are generally low viscosity, fluid-like solutions that permit mixing with cells and/or bioactive factors and may be polymerized or crosslinked in situ. While several in situ crosslinkable materials have been evaluated for cartilage repair in vivo, only a few have been prepared from natural biomaterials including collagens, chitosans, alginates, and hyaluronans (Lee, et al. Biomaterials, 2001, Chenite, et al. Biomaterials, 2000, 21(21) pp. 2155-61; Paige, et al. Plast Reconstr Surg, November 1995, 96(6) pp. 1390-8 and Nettles, et al. Ann Biomed Eng., March 2004, 32(3) pp. 391-7).

In prior work, biomaterials containing polypeptide sequences native to elastin have been shown to promote chondrocyte survival and cartilage matrix biosynthesis in vitro for primary chondrocytes, invertebral disc cells and for stem cells isolated from adipose tissue (Betre, et al. Biomacromolecules, September-October 2002, 3(5) pp. 910-6; Knight, et al. Trans. SFB, 2003; Betre, et al. Trans ORS, 2004). Elastin-based sequences may be crosslinked by multiple means, with evidence that the crosslinked systems do not interfere with chondrocyte survival and matrix deposition (Cappello, et al. J Control Release, 1998, 53(1-3) pp. 105-17, Cappello, Handbook of Biodegradable Polymers, 1997, Knight, et al Trans. SFB, 2003).

Synovial fluid in an injured joint is known to contain many factors which have an influence on the progression of osteoarthritis (see, for example, Fernandes, et al., "The Role of Cytokines in Osteoarthritis Pathophysiology", Biorheology, 39 (1-2): 237-246, 2002). Cytokines, such as Interleukin-1 (IL-1) and Tumor Necrosis Factor-$\alpha$ (TNF-$\alpha$), which are produced by activated synoviocytes, are known to upregulate matrix metalloproteinase (MMP) gene expression. Currently, research is aimed at finding biochemical agents that can neutralize this upregulation. Research is also being aimed at finding stimulatory agents to compensate for the deleterious effects of this upregulation. Such stimulatory agents include, for example, transforming growth factors (e.g., TGF-$\beta$) or insulin like growth factor (IGF-1).

The repair of cartilage defects is believed to be impaired by the same factors in synovial fluid as influence the degeneration of cartilage in osteoarthritis. In view of this, it would be advantageous to provide a cartilage repair technique, which involves producing a barrier against synovial fluid at the defect site. The barrier would seal the cartilage defect against synovial fluid and the deleterious factors therein. In this way, the healing wound could be temporarily protected.

It would also be advantageous if the use of a barrier against synovial fluid had application in all synovial joint tissues. For example, migration of synovial fluid into the tunnel of cruciate ligament grafts has been implicated in the post surgery tunnel widening phenomena which is observed. In view of this, it would be advantageous to provide a ligament grafting technique, which involves producing a barrier against synovial fluid ingress into the bone tunnels. The barrier would seal the bone tunnels against synovial fluid and the deleterious factors therein.

It is currently not possible to effectively repair torn ligaments that are within the synovial capsule. It is likely that a factor responsible for this is the influence of synovial fluid, and the factors within it, on the healing process. Therefore, there is a need for an improved method of repairing torn or damaged ligaments, which involves creating a barrier between the damaged ligament and the synovial fluid.

SUMMARY OF THE INVENTION

The present invention provides a composite tissue formed in situ. This composite tissue includes a synovial joint tissue; and a barrier material adhered thereto for sealing the synovial joint tissue against synovial fluid.

The present invention also provides a barrier system. This barrier system is formed as a polymeric coating on a synovial joint tissue surface by applying a curable protein copolymer solution to the synovial joint tissue surface; and curing the protein copolymer in situ, thereby forming an effective barrier on the synovial joint tissue surface against synovial fluid.

In some embodiments, the synovial joint tissue includes a defect, which is fillable and sealable by the barrier material. The barrier material excludes synovial fluid from the defect. The present inventors have found that, by providing a barrier that excludes synovial fluid from the defect, a superior healing response is obtained as compared to untreated defects.

For example, the invention provides a method for regenerating synovial joint tissue in situ by excluding synovial fluid therefrom. The method includes providing a synovial joint tissue having a defect; and placing a barrier material in intimate contact with the defect for sealing the defect against synovial fluid. The barrier material includes a curable protein copolymer. The method further includes curing the protein copolymer in situ.

Also provided is a method of treating a wound in synovial joint tissue. The method includes applying (i) a crosslinkable protein copolymer including recombinant elastin and fibroin polymer chains; and (ii) a crosslinker to the tissue in the presence of synovial fluid. The method also includes allowing the recombinant elastin and fibroin polymer chains to crosslink, thereby forming an adherent barrier coating on the tissue. The coating excludes at least a portion of the synovial fluid from the tissue. The method further includes permitting autologous cells to infiltrate the wound beneath the barrier coating to improve regenerative healing.

The present invention also provides a method of repairing a cartilage defect. This method includes applying a curable protein copolymer solution to a cartilage defect treatment site. The method also includes curing the protein copolymer in situ, thereby forming an effective barrier at the treatment site, which barrier temporarily excludes synovial fluid from the cartilage defect to promote repair thereof.

The present invention further provides a method of repairing a torn cruciate ligament. The method includes encapsulating the torn cruciate ligament in a barrier material, which barrier material temporarily seals the torn ligament against synovial fluid to promote repair thereof.

DETAILED WRITTEN DESCRIPTION OF THE INVENTION

As described above, synovial fluid in an injured joint is known to contain many factors which negatively influence the repair of synovial joint tissue. In particular, factors, including cytokines, such as IL-1 and TNF-α, which are produced by activated synoviocytes, are known to upregulate matrix metalloproteinase (MMP) gene expression. This upregulation inhibits wound healing.

In the present invention, an adhesive barrier material is used to temporarily exclude synovial fluid from the site of injury where a healing response is required. For example, in one embodiment, the synovial joint tissue has a defect sealable by the barrier material. The barrier material is capable of flowing into the defect, such as a knee cartilage defect. Upon curing, the barrier material is adhered to the defect, causing a barrier to be formed between the defect and the synovial fluid. The barrier forms a temporary shield to protect the healing wound following treatment.

Protein Polymers

In one desired embodiment, the barrier material includes a crosslinked network, or a self gelled network of repeating elastin-like and fibroin-like polymer chains. The elastin-like and fibroin-like polymer chains can be chemically crosslinked. Alternatively, the elastin-like and fibroin-like polymer chains self-associate to form a gel.

In one embodiment, the repeating fibroin-like polymer chains of the barrier material include the sequence GAGAGS (SEQ ID NO:1). Moreover, in one embodiment, the repeating elastin-like polymer chains of the barrier material include the sequence GVGVP (SEQ ID NO:2).

At least one amino acid in the repeating fibroin-like and/or elastin-like polymer chains can be modified to provide for an appropriate number of functionalities in the polymer(s) for crosslinking. In one embodiment, at least some of the elastin-like polymer chains are modified by replacement of an amino acid with a substitute amino acid that serves as a site of the crosslinking. In a preferred embodiment, a valine in the elastin-like polymer chain is substituted with a lysine. For example, the repeating elastin-like polymer chains of the barrier material can include the sequence: GKGVP (SEQ ID NO:3), wherein K serves as a crosslinking site. In this instance, the amino functionality on the lysine is available for crosslinking.

For the most part, the polymers of the subject invention will have the active functionality of a naturally occurring amino acid in the chain of the polymer. For example, the functionalities for crosslinking may include amino (e.g., lysine), carboxyl (e.g., aspartate and glutamate), guanidine (e.g., arginine), hydroxyl (e.g., serine and threonine), and thiol (e.g., cysteine). Alternatively, pendant groups may be employed to provide the desired functionalities for crosslinking. For example, carboxyl groups may be reacted with polyamines so as to exchange a carboxyl functionality for a single amino or plurality of amino groups. An amino group may be substituted with a polycarboxylic acid so that the amino acid will be replaced with a plurality of carboxylic groups. A thiol may be replaced with an aldehyde by reaction with an aldehydic olefin so as to provide for an aldehyde functionality. By appropriate choice of the functionality on the protein polymer, and the crosslinking agent, rate of reaction and degree of crosslinking can be controlled.

Suitable protein polymers for use in the present invention and methods of preparing them are described in the following U.S. Pat. Nos. 5,770,697, 6,018,030, 6,355,776, 6,423,333, 6,380,154, 5,817,303, 6,033,654 and 5,235,041, which are incorporated herein by reference in their entirety. Moreover, the following U.S. patent Nos. describe synthetic genes useful in the preparation of suitable protein polymers for purposes of the present invention: U.S. Pat. Nos. 5,243,038, 6,184,348 and 6,140,072, which are incorporated herein by reference in their entirety.

In one preferred embodiment, the curable copolymer used to form the barrier against synovial fluid at the injury site is Polymer 27K. This is a synthetic protein copolymer comprised of two specific amino acid sequences, or blocks, homologous to natural silk fibroin and human elastin protein segments. This polymer is described, for example, in U.S. Pat. Nos. 5,817,303 and 6,033,654, where it is referred to as SELP0K.

In the present invention, Polymer 27K is suitable for use in forming a barrier at the site of injury in a synovial joint. The barrier temporarily excludes synovial fluid from the injury site to permit regeneration of the tissue.

Polymer 27K is a sequential block copolymer composed of amino acids. The synthetic silk segment is a repeat unit duplicating that found in natural silk fibroin, and consists of a sequence of six amino acids: glycine-alanine-glycine-alanine-glycine-serine [GAGAGS], which corresponds to SEQ ID NO:1. The synthetic elastin segment is a repeat unit identical to that found in human elastin, and consists of a sequence of five amino acids: glycine-vline-glycine-valine-proline [GVGVP], which corresponds to SEQ ID NO:2. The polymer designation "27K" refers to the number of these sequences in each repeating component of the copolymer (i.e., two blocks of silk, seven blocks of elastin). The "K" designates that a modified elastin block, where a valine has been substituted with a lysine, is also present. This modified elastin block has the following sequence: GKGVP (SEQ ID NO:3). The 27K copolymer amino acid sequence can be represented by the following formula:

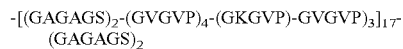

Amino acids representing silk blocks and amino acids representing elastin blocks account for about 22.8% and 71.7%, respectively, of the total copolymer, by number. The ratio of silk blocks to elastin blocks is about 1:4.

Amino-terminus "head" and carboxy-terminus "tail" sequences of 33 and 19 amino acids, respectively, complete Polymer 27K. The amino acids representing head and tail units account for about 5.5% of the total copolymer, by number.

Polymer 27K is represented graphically as follows:

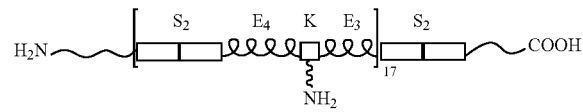

where S represents a silk block with the amino acid sequence GAGAGS (SEQ ID NO:1) and E represents an elastin block with the amino acid sequence GVGVP (SEQ ID NO:2). K represents a modified elastin block with the amino acid sequence GKGVP (SEQ ID NO:3), and serves as a site of chemical crosslinking. There are seventeen (17) tandem repetitions of the copolymer structure in Polymer 27K. The head component consists of the amino acid sequence MDPVVLQRRDWENPGVTQLNRLAAHPPFASDPM (SEQ ID NO:4), and the tail consists of the sequence GAMDPGRYQDLRSHHHHHH (SEQ ID NO:5). $H_2N$ represents the amino terminus of the polypeptide chain and $NH_2$ is the epsilon amino group of the lysine side chain. COOH represents the carboxyl terminus of the polypeptide chain.

Polymer 47K is another example of a suitable protein polymer for use in the present invention. Polymer 47K is described in U.S. Pat. Nos. 6,380,154 and 5,817,303, where it is referred to as SELP8K. This protein polymer may be prepared in accordance with the methods described in U.S. Pat. Nos. 5,243,038 and 5,817,303, for example. The elastin-like and fibroin-like polymer chains in Polymer 47K self-associate to form a gel.

One skilled in the art will recognize that any polymer system capable of curing in situ and forming an adhesive bond with tissue and creating a barrier film would have utility in this invention. Such materials include, but would not be limited to, polyurethanes, polyacrylates and cyanoacrylates.

For example, in one embodiment, the barrier material includes an in situ curable acrylate polymer, including cyanoacrylate. In another embodiment, the barrier material includes an in situ curable polyurethane.

Usually, the polymer will be available as a dispersion or solution, particularly aqueous. Generally, the concentration of the protein polymer will be in the range of about 50 mg/ml to 1 g/ml, more usually from about 100 mg/ml to 800 mg/ml. The solution may be buffered at a pH which enhances or retards cure. Usually, the pH will be in the range of about 2 to about 12, more usually in the range of 8 to 11. Various buffers may be used, such as phosphate, borate, carbonate, etc.

The protein composition will generally be about 5 to 40, more usually from about 5 to 20, preferably from about 10 to 20 weight %, to provide for a composition which may be readily handled, will set up within the desired time limit, and the like. The buffer concentration will generally be in the range of about 50 to 500 mM. Other components may be in the protein composition, including biologically active agents, etc. Such other components are described in further detail below.

Chemical Crosslinkers

As described above, in one embodiment, the barrier material includes a crosslinked network of polymer chains. In particular, the curable protein copolymer can cure in situ through crosslinking of the protein polymer chains.

Various crosslinking agents may be employed, particularly those which have been used previously and have been found to be physiologically acceptable. Crosslinking agents which may be used include dialdehydes, such as glutaraldehyde, activated diolefins, diisocyanates, such as, tetramethylene diisocyanate, hexamethylene diisocyanate, octamethylene diisocyanate, acid anhydrides, such as succinic acid dianhydride, ethylene diamine tetraacetic acid dianhydride, diamines, such as hexamethylene diamine, cyclo(L-lysyl-L-lysine), etc. The crosslinking agents are usually commercially available, or may be readily synthesized in accordance with conventional ways, either prior to application to the synovial joint tissue or by synthesis in situ.

In one embodiment of the present invention, the chemical crosslinker is an isocyanate. In one preferred embodiment, the chemical crosslinker is hexamethylene diisocyanate, which is commonly abbreviated in the literature as either HMDI or HDI. It is a monomeric aliphatic difunctional isocyanate. HMDI includes a linear, saturated hydrocarbon backbone six carbons long ($-CH_2-CH_2-CH_2-CH_2-CH_2-CH_2-$), capped at each end with isocyanate group ($-N=C=O$). It is available by various fine chemical producers and distributors, such as Sigma-Aldrich, Fluka, Pfaltz & Bauer, etc.

The ratio of crosslinking agent to polymer will vary depending upon the crosslinking agent, the number of functionalities present on the polymer, the desired rate of curing, and the like. Generally, the weight ratio of polymer to crosslinking agent will be at least about 1:1 and not greater than about 100:1, usually not greater than about 50:1. However, the weight ratio of polymer to crosslinking agent is generally in the range of about 20 to 50:1.

Other Components

As described above, in one embodiment, the protein polymer includes a functional group capable of reacting with a crosslinking agent. This allows for the formation of a strongly adherent adhesive composition for bonding to and sealing tissue defects. The barrier material can also include other tissue adhesives. For example, in one embodiment of the present invention, the barrier material includes a cyanoacrylate. Other examples of tissue adhesives that can be included in the barrier material include gelatin-aldhehyde type or fibrin glue type adhesives. Tissue adhesives are described in: Tissue Adhesives in Surgery, Matsumoto, T., Medical Examination Publishing Co., Inc. 1972 and Sierra, D. H., J. Biomat. App. 7:309-352, 1993.

If desired, the subject compositions may be prepared with various extenders or extending agents. Such extenders can be combined with the protein polymer and/or the crosslinking agent. The extenders may modulate the setting time and provide for desirable physical or physiological properties of the barrier material.

Such extenders, when employed, will usually not exceed 50 weight percent of the barrier composition, and will generally not exceed about 20 weight percent. More usually, extenders will not exceed about 10 weight percent. Extenders which may be employed in the barrier material include, but are not limited to, synthetic polymers, both addition and condensation polymers, both protein and non-protein, such as polylactides, polyglycolides, polyanhydrides, polyorthoesters, polyvinyl compounds, polyolefins, polyacrylates, polyethylene glycol, polyesters, polyvinyl alcohol, polyethers, copolymers and derivatives thereof. Suitable extenders for use in the present invention further include, but are not limited to naturally occurring polymers, such as proteins and nonproteins, including collagen, fibrinogen, fibronectin, laminin, keratin, chitosan, heparin, dextran, alginates, cellulose, glycosoaminoglycans, hyaluronic acid, polysaccharides, derivatives thereof, and the like.

In one embodiment, the barrier material includes seed cells. Preferably, the seed cells are cartilage repair cells. "Cartilage repair cells" as used herein refers to a cell which, when exposed to appropriate stimuli, will differentiate and be transformed into a chondrocyte. Cartilage repair cells include mesenchymal cells, fibroblasts, fibroblast-like cells, macrophages, and dedifferentiated chondrocytes. In one preferred embodiment of the present invention, the seed cells are chondrocytes and/or mesenchymal stem cells. The seed cells may be autologous cells (i.e., from the patient's own body), which can assist in the repair of the synovial joint tissue injury.

Therapeutic cells can be encapsulated within the protein polymer when in cures in situ (i.e., when it is crosslinked or gels in situ). For example, the polymer compositions of the present invention are fluid-like solutions that permit mixing with cells. Alternatively, micropellets of cells or sheets of tissue engineered cartilage can be placed in a defect, and held in place and shielded from synovial fluid by a covering layer of the barrier material. Healing would then be allowed to occur. In either case, the cells propagate and grow after being implanted and form tissues leading to repair of the defective synovial joint tissue.

In one embodiment, the barrier material provides attachment and growth of autologous chondrocytes. In another embodiment, the barrier material provides attachment and growth of autologous mesenchymal stem cells.

In one preferred embodiment, chondrocytes are removed from the patient, expanded in culture, and are reimplanted in the patient at the site of the tissue defect. In one example, the cells, curable protein polymer and a crosslinking agent are delivered to the defect site, and the cells are held in place when the protein polymer cures in situ. Alternatively, the chondrocytes are placed in a defect, and held in place by a covering layer of the barrier material.

In another preferred embodiment, the microfracture technique can be used to access pluripotential mesenchymal cells in the underlying bone marrow. The surgeon creates holes through the subchondral bone into the underlying cartilage. The holes allow stem cells from the bone marrow to enter the defect site. The cells released into the defect site can be held at the defect site and shielded from the synovial fluid by a covering layer of the barrier material, cured in situ. Alternatively, the cells can be encapsulated within the barrier material upon cure.

In a further preferred embodiment, the use of the barrier material can be combined with a technique, such as Mosaicplasty™. In this technique, plugs of cartilage and bone are taken from the periphery of the joint and placed in the defect site. It is well within the contemplation of the present invention that these plugs can have a covering layer of the barrier material In another embodiment, the barrier material includes a biologically active agent. For example, the biologically active agent can be a growth factor and/or a cytokine, or other tissue regeneration medicine. It is possible, for example, to include biologically active materials within the barrier material, such as polysaccharides, proteins, peptides, genes, antigens and antibodies. Such biologically active materials could be used to attract the patient's own cartilage repair cells to the defect site. For example, a particular antibody incorporated into the barrier material could be used to bind to a receptor present on chondrocytes. Once at the defect site, the cells form tissues leading to repair of the defect.

Other biologically active agents that can be incorporated into the barrier material include, but are not limited to, antibiotics, antivirals, antiinflammatories, both steroidal and non-steroidal, enzymes and enzyme inhibitors, anticoagulants and/or antithrombotic agents, compounds modulating cell migration, proliferation and/or growth, transforming factors, anti-angiogenic agents, vasodilating agents, and other drugs commonly used for the treatment of injury to tissue.

It is noted that proliferative agents can stimulate the proliferation of cartilage repair cells. Moreover, a proliferative agent can serve as a chemotactic agent to attract cartilage repair cells to the injury site. Agents useful for proliferating cartilage repair cells are known and include, for example, transforming growth factors, insulin-like growth factors, acidic or basic fibroblast growth factors, platelet derived growth factors, epidermal growth factors and hemopoietic growth factors.

A transforming factor or factors may be present in the barrier material at a concentration sufficient to promote differentiation of cartilage repair cells into chondrocytes, which form new stable cartilage tissue. Transforming factors include, but are not limited to, transforming growth factors α and β, fibroblast growth factors and bone morphogenic proteins.

Methods of Preparing Protein Polymer Compositions

Polymers for use in the present invention may be prepared in accordance with the methods described in U.S. Pat. Nos. 5,235,041, 5,243,038, 6,184,348, 6,140,072, 6,033,654 and 6,423,333. For example, Polymer 27K (MW of 76,639 daltons) is produced by constructing, from synthesized DNA, a gene encoding the complete protein sequence, having specified repeat sequences, number and periodicity.

One procedure involves chemically synthesizing small segments of complimentary single-stranded DNA (ssDNA) oligomers of from about 15 to 150 nucleotides and annealing the ssDNA oligomers to form one or a plurality of double-stranded DNA (dsDNA) fragments having cohesive ends. Through successive cloning steps, one or more of these fragments are ligated together to form a segment or a plurality of segments, which in turn are ligated together to form a monomer sequence. The fragments may be the same of different. Cloning vectors are used which allow for selective digests of the dsDNA fragments with the appropriate termini for subsequent ligations. In one example, one segment of the monomer sequence was created using a chemically synthesized ssDNA oligomer amplified using the polymerase chain reaction. The monomer sequence then becomes the major repeating block of the polymer gene. At each cloning step, the double-stranded DNA sequences can be verified by DNA sequencing to ensure the sequence integrity is retained. The construction of these synthetic genes and their use in polypeptide synthesis is described in U.S. Pat. Nos. 5,243,038 and 6,423,333, and PCT/US96/06229, the disclosures of which are herein incorporated by reference.

Once the polymer gene having blocks of repetitive units has been prepared, the gene is then expressed in a recombinant *Escherichia coli* (*E. coli*) host. In one embodiment, all *E. coli* competent cells used, including the strain to produce the production cell bank, are *E. coli* strain K12 derivatives. The resulting protein is preferably purified in accordance with conventional methods and formulated with buffers, excipients and the like into a fluid, which can be prefilled in a container such as a syringe or vial and stored in a liquid, frozen or lyophilized state.

In one example, a cell line expressing Polymer 27K (P27K) is first produced via recombinant DNA techniques in bacterial fermentation and the cells are frozen. The manufacturing process then consists of expansion of an aliquot of frozen cells from a qualified cell bank via fermentation, induction of protein expression followed by biomass harvest. P27K is purified from the biomass by cellular lysis, removal of cellular debris by polyethylene imine precipitation and centrifugation, removal of impurities by ammonium sulfate precipitation, cation exchange chromatography and then anion exchange chromatography. Purified P27K is then diafiltered and concentrated to the desired final protein concentration and buffer formulation by diafiltration, ultrafiltration and vacuum evaporation.

P27K purification is described in WO 96/34618, where it is referred to as SELPOK. WO 96/34618 is incorporated herein by reference. Other suitable methods for purifying recombinant proteins are described, for example, in Guide to Protein Purification Deutscher M. P. (Ed.), Methods Enzymol. 182, Academic Press Inc., New York (1990) and in Protein Purification (Third Edition), Scopes, R. K. and Cantor, C. R. (Eds), Springer-Verlag, New York (1994).

Preparation of the Crosslinker

As described above, various crosslinking agents may be employed, particularly those which have been used previously and have been found to be physiologically acceptable. In one preferred embodiment, the crosslinker, which is combined with the Polymer 27K composition, is hexamethylene diisocyanate, which is commonly abbreviated in the literature as HMDI.

HMDI source material can be purchased from Sigma-Aldrich Fine Chemicals, Saint Louis, Mo.; catalog No. D124702. This material is sterile-filtered, aseptically packaged in pre-sterilized Type I amber glass vials. The vialed HMDI crosslinker is stored at 2-40° C. until use.

Preparation of a Barrier Material

The polymer (e.g., Polymer 27K) and a suitable crosslinker (e.g., HMDI) can be combined using accessory mixing equipment to create a mixture that transforms from a liquid into a crosslinked network of polymer chains in situ. The Polymer 27K and the HMDI components are preferably combined on a volume basis in a ratio of about 127:1, yielding a mixture composition of 99.2% Polymer 27K and 0.8% of the HMDI crosslinker. The molar ratio of isocyanate to amine in the mixture is about 2.04:1. Gelation from the liquid state derives from chemical crosslinking between isocyanate groups of the HMDI crosslinker and amino groups of Polymer 27K.

The protein polymer and the crosslinking agent may be prepared prior to use, where one or both may have extenders, or one of the other components described herein (e.g., biologically active agent). The protein polymer and the crosslinker may be readily mixed in accordance with conventional ways. For example, syringes can be used. The syringes can inject the ingredients into a central chamber and the components mixed by drawing the fluid back and forth. Alternatively, the protein polymer and the crosslinker may be dispensed simultaneously at the site of application.

In other embodiments of the present invention, the chains of the protein polymer self-associate to form a gel. For example, when Polymer 47K is employed, the barrier material includes a self gelled network of repeating fibroin-like and elastin-like polymer chains. In such embodiments, a chemical crosslinker would not be required.

Tissue Surfaces to be Treated and Application to the Tissue

The subject compositions of the present invention may be applied to any synovial joint tissue in need of repair. In one embodiment, the synovial joint tissue is cartilage. In another embodiment, the synovial joint is the knee. In still another embodiment, the synovial joint is the facet joint of the spine. However, the present invention is not limited to the treatment of cartilage defects in these synovial joints. It has application in all synovial joints.

The present invention is also not limited to the treatment of joint cartilage. For example, in one embodiment of the present invention, the barrier material is used to encapsulate a torn cruciate ligament (e.g., anterior or posterior cruciate ligament). The barrier material temporarily seals the torn ligament against synovial fluid to promote repair thereof. In some embodiments, additional mechanical support is given to the torn ligament to allow the ligament to heal naturally.

For example, the mechanical support can include sutures. For example, small bores can be drilled in the adjacent bones approximately at the anatomically correct sites for normal connection of the cruciate ligament. Multiple loops of suture are then used for reconnecting the ligamentous stumps to the bone. The curable protein polymer and crosslinker can then be applied to encapsulate the sutured ligamentous stumps.

In another embodiment, the mechanical support is an augmentation device, such as an artificial augmenting strip or sleeve. Such devices are known in the art. For example, strips or bands of Dacron, polyethylene or carbon fiber have been used across the repair site. Typically, their opposite ends are sutured or otherwise anchored to the ligament remote from the injury to provide the primary or secondary support for the healing ligament. The barrier material can be used to encapsulate the torn portion of the anchored ligament.

Also, the ends of a torn ligament can be enclosed in a hollow sleeve to support healing of the ligament. The adjacent ligament ends are secured inside the sleeve, such as by suturing. By encapsulating the torn portion of the ligament in the barrier material, healing is promoted.

It is noted that the current standard of care for a torn ligament is to replace it with autograft or allograft tissue. Migration of synovial fluid into the tunnel of cruciate grafts has been implicated in the post surgery tunnel widening phenomena which is observed. In the present invention, the barrier material could be used to seal to tunnel ends and prevent synovial fluid migration.

The subject compositions may be applied to any synovial joint tissue in any convenient way, for example, by using a syringe, catheter, cannula, manually applying the composition, spraying, or the like. Polymer 27K takes an initial set (ca. 63% of ultimate modulus) five minutes after mixing, and reaches 95% of its ultimate cure modulus 30 minutes after mixing. The crosslinking of the polymer produces no measurable temperature change during cure.

To carry out the methods of treating defects in cartilage according to this invention, a defect is identified, prepared and filled with the compositions according to this invention. Cartilage defects in animals, such as humans, are readily identifiable visually during arthroscopic examination of the joint or during simple examination of the lesion or defect during open surgery. Cartilage defects may also be identified inferentially by using magnetic resonance imaging (MRI) analysis, physical examination or by any other procedure known in the art. The same procedures can be used to identify defects (e.g., lacerations and tears) in ligaments.

Once a defect in cartilage or a ligament has been identified, the surgeon may elect to surgically modify the defect to enhance the ability of the defect to physically retain the compositions that are added in the treatment methods described herein. For example, preferably, for a cartilage defect, instead of having a flat or concave geometry, the defect has or is shaped to have vertical edges or is undercut in order to better retain the compositions added in the treatment methods described herein. Additionally, for a cartilage defect a source of repair cells is preferably provided by drilling or microfracture of the subchondral bone.

For cartilage repair, preferably, the defect is completely filled with the barrier material. This can be accomplished, for example, by injection of a curable protein polymer into the defect with a syringe. As described herein, the barrier material preferably includes a cross-linked or self-gelled network of fibroin-like and elastin-like polymer chains. In one embodiment, a curable polymer is mixed with a crosslinker and deposited into the defect site with a syringe. The barrier material can also include other components, such as cartilage repair cells and/or biologically active agents.

For ligament repair, a laceration can be completely covered with the barrier material by injection of a curable protein polymer onto the surface of the laceration with a syringe. In one embodiment, a curable polymer described herein is mixed with a crosslinker and deposited at the ligament injury site. Other components can be deposited also, such as cells or a biological agent.

If the ligament is torn, approximation of the torn surfaces of the tissue can be achieved mechanically with sutures, strips or sleeves, according to methods known in the art. The torn surfaces can then be encapsulated within the barrier material to prevent synovial fluid from migrating into the area of the injury. In so doing, the rejoining of the ligament tissue is promoted. In one embodiment, the in situ gelling or crosslinking biomaterials described herein can be deposited at the ligament tear site with a syringe.

EXAMPLES

Example 1

Methods

Protein Synthesis

Copolymers of silk and elastin-containing peptide sequences were prepared with 2 silk and 7 (unmodified) elastin blocks per polymer repeat (NuCore™ Injectable Polymer, SpineWave, Shelton, Conn.) and synthesized using recombinant DNA technology (*E. coli* K12). One elastin block was modified to provide for chemical cross-linking via a polyfunctional diisocyanate-based cross-linking agent. The copolymer synthesized is referred to herein as Polymer 27K.

The copolymer was prepared in accordance with the methods described in U.S. Pat. Nos. 5,235,041, 5,243,038, 6,184,348 and 6,140,072. When mixed at low relative ratios of crosslinker-to-polymer, the material will substantially set within 5 minutes and reach complete crosslinking within ~30 minutes. Aqueous solutions of polymer were prepared (19.3% w/v protein, pH 7.1) and evaluated for dynamic shear properties (magnitude of complex modulus G* =26 kPa). Standard biocompatibility and toxicology testing of the polymer-crosslinker system has been performed, and the material was determined to be non-cytotoxic, non-irritating and non-toxic in all evaluations.

Animal Model of an Osteochondral Defect

In this study, an injectable copolymer (Polymer 27K) of peptide sequences native to both silk and elastin was chemically crosslinked and evaluated for the first time as a defect-filling scaffold to promote cartilage repair in a rabbit osteochondral defect model. The objectives of this study were to determine the ability of the scaffold to promote cell infiltration, new matrix synthesis, and tissue integration, as well as to evaluate the handling characteristics of the polymer for cartilage repair.

Osteochondral defects (3 mm dia.×1.5 mm depth) were created bilaterally at approximately 6 mm distal to the intercondylar notch on the medial femoral condyles of 4 month-old New Zealand White rabbits (n=5). Polymer was dynamically mixed with the polyfunctional cross-linker and deposited into the defect site via a 18 g syringe (total volume ~0.5 ml). The polymer was permitted to set into a turgid hydrogel for ~5 minutes, after which the joint was closed. Defects in the right knees were left unfilled and served as controls. Animals were allowed free cage activity after surgery until sacrifice at four (n=2) or twelve weeks (n=3).

Histology and Immunohistochemistry

Joints were harvested and cartilage-bone samples were processed for histology. Cryostat sections were prepared (7 microns) and stained with H&E safranin O, and Masson's trichrome. A semi-quantitative grading scheme adapted from the ICRS Cartilage Injury Evaluation Package was used to evaluate cellularity, proteoglycan and matrix staining, and integration of the repair tissue (0=no evidence of repair to 12-normal cartilage matrix). In sections prepared from joints harvested at 12-weeks post-surgery, additional immuno-histochemical staining was done to detect the presence of type I and type II collagen (0=no evidence of repair to 18=cartilage matrix). Accordingly, the histological grading scores reflect the inclusion of the immuno-histochemical stained sections at the 12-week timepoint only. All stained sections were evaluated by three blinded graders.

Example 2

Results

At 4 weeks, both control and polymer-filled osteochondral defects appeared to be largely filled with a white, slightly roughened tissue. Cells in the polymer-filled joints appeared viable on H&E stained sections, although the total number of cells was generally less in the joint defects filled with the polymer. There was some evidence of less bony healing and reduced proteoglycan-staining on trichrome-stained sections of the polymer-filled defects at 4 weeks, as compared to the unfilled controls. This result may be related to the lower numbers of cells observed in the polymer at this timepoint. By 12 weeks, there was evidence of improved healing in the polymer-filled defects, as compared to the unfilled controls, with evidence of bony and adjacent cartilage integration, an intact articular surface, and the absence of fibrous tissue formation. Polymer-filled defects also stained positively for type II collagen in all joints with little to no presence of staining for type I collagen. Indeed, total grades for histological appearance were higher for those defects filled with the polymer (13.8±1.9 vs. 12.3±1.1 for controls).

These results show the effect of the crosslinked polymer scaffold on cell-driven tissue regeneration and polymer integration in an osteochondral defect. By 12 weeks, cells were able to infiltrate the polymer scaffold, remain viable and synthesize a type II collagen and proteoglycan-containing matrix. Overall, the in situ crosslinked polymer was highly attractive for the ability to simply and quickly fill defects in a living animal, with a native material prepared in an aqueous environment.

What is claimed is:

1. An in situ method of treating a wound in synovial joint tissue comprising the steps of:
   (a) applying to the tissue in the presence of synovial fluid:
      (i) a crosslinkable protein copolymer comprising recombinant elastin and fibroin copolymer chains; and
      (ii) a crosslinker;
   (b) allowing the recombinant elastin and fibroin copolymer chains to crosslink in situ, thereby forming an adherent barrier coating on the synovial tissue surface, wherein the coating excludes at least a portion of the synovial fluid from the tissue, and forms an effective barrier on the synovial joint tissue surface against synovial fluid wherein said coating exclusion results in formation of the barrier coating, and
   (c) seeding the barrier coating with autologous cells which promote the wound healing and permit said cells to infiltrate the wound beneath the barrier coating to improve regenerative healing.

2. The method of claim 1, wherein the crosslinker is an isocyanate.

3. The method of claim 2, wherein the isocyanate is hexamethylene diisocyanate.

4. The method of claim 1, wherein applying includes injection into a site of the wound.

5. The method of claim 1, further including accessing pluripotential mesenchymal stem cells in bone proximal to the wound.

6. The method of claim 1, wherein the synovial joint tissue is cartilage.

7. The method of claim 1, wherein the synovial joint tissue is a ligament.

8. The method of claim 1, wherein a synovial joint tissue is the facet joint of the spine.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial sequence
<220> FEATURE:
<223> OTHER INFORMATION: synthetic peptide

<400> SEQUENCE: 1

Gly Ala Gly Ala Gly Ser
1               5

<210> SEQ ID NO 2
<211> LENGTH: 5
<212> TYPE: PRT
<213> ORGANISM: Artificial sequence
<220> FEATURE:
<223> OTHER INFORMATION: synthetic peptide

<400> SEQUENCE: 2

Gly Val Gly Val Pro
1               5

<210> SEQ ID NO 3
<211> LENGTH: 5
<212> TYPE: PRT
<213> ORGANISM: Artificial sequence
<220> FEATURE:
<223> OTHER INFORMATION: synthetic peptide

<400> SEQUENCE: 3

Gly Lys Gly Val Pro
1               5

<210> SEQ ID NO 4
<211> LENGTH: 33
<212> TYPE: PRT
<213> ORGANISM: Artificial sequence
<220> FEATURE:
<223> OTHER INFORMATION: synthetic peptide

<400> SEQUENCE: 4

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met

<210> SEQ ID NO 5
<211> LENGTH: 19
<212> TYPE: PRT
<213> ORGANISM: Artificial sequence
<220> FEATURE:
<223> OTHER INFORMATION: synthetic peptide
```

```
-continued

<400> SEQUENCE: 5

Gly Ala Met Asp Pro Gly Arg Tyr Gln Asp Leu Arg Ser His His His
1               5                   10                  15

His His His
```